United States Patent [19]

Golovanivsky et al.

[11] Patent Number: 5,355,399
[45] Date of Patent: Oct. 11, 1994

[54] PORTABLE X-RAY SOURCE AND METHOD FOR RADIOGRAPHY

[75] Inventors: Konstantin S. Golovanivsky, Antony, France; Valeri D. Dugar-Zhabon, Moscow, Russian Federation

[73] Assignee: Ruxam, Inc., New York, N.Y.

[21] Appl. No.: 935,528

[22] Filed: Aug. 25, 1992

Related U.S. Application Data

[63] Continuation-in-part of Ser. No. 843,569, Feb. 28, 1992.

[51] Int. Cl.$^5$ ............................................ H01J 35/00
[52] U.S. Cl. .................................... 378/119; 378/210
[58] Field of Search ........................................ 378/119

[56] References Cited

U.S. PATENT DOCUMENTS 4,553,256 11/1985 Moses ................................. 378/137
4,952,273 8/1990 Popov ................................. 156/643

OTHER PUBLICATIONS

Garner et al "An Inexpensive X-ray Source Based On An Electron Cyclotron" *Rev. Sci Instrum,* 61(2), Feb. 1990, pp. 724–727.
Blumenthal "Food Irradiation Toxic to Bacteria, Safe For Humans" *FDA Consumer,* Nov. 1990, pp. 11-15.
Brynjolfsson "Factors Influencing Economic Evaluation Of Irradiation Processing" *Factors Influencing The Economical Application Of Food Irradiation Symposium Proceedings, 14–18 Jun. 1971,* 1973, pp. 13–35.
Popov "Electron Cyclotron Resonance Plasmas Excited By Rectangular and Circular Microwave Modes" *J.V. Sci. Technical A* 8(3) May/Jun. pp. 2909–2912.
Popov et al., "Microwave Plasma Source For Remote Low Energy Ion Stream" *Rev. Sci. Instrum.,* 61(1), Jan. 1990 pp. 300–302.
Popov et al., "Electron Cyclotron Resonance Sources For Wide and Narrow Plasma Streams", *Rev. Sci. Instrum.,* 61(1), Jan. 1990 pp. 303–305.
Cleland et al. "Electrons Versus Gamma Ray-Alternative Sources For Irradiation Process" *Food Irradiation Processing Symposium Proceedings* 4–8 Mar. 1985, pp. 397–406.
Lagunas-Solar "New Considerations For Radiation Technology Transfer Programmes For Developing Countries", *Food Irradiation Symposium Proceedings* 4–8 Mar. 1985, pp. 499–506.
Popov et al., "Electron Cyclotron Resonance Plasma Stream Source For Plasma Enhanced Chemical Vapor Deposition" *J. Vac. Technol. A*7(3) May/Jun. 1989 pp. 914–917.

(List continued on next page.)

*Primary Examiner*—Craig E. Church
*Attorney, Agent, or Firm*—Davis Hoxie Faithfull & Hapgood

[57] ABSTRACT

A small, low cost, low power, and portable x-ray source that produces an x-ray flux that is sufficient to produce high quality x-ray images on suitable x-ray sensitive films. The source includes a vacuumated chamber that is filled with a heavy atomic weight gas at low pressure and an x-ray emitter. The chamber is in a magnetic field and an oscillating electric field and generates an Electron Cyclotron Resonance (ECR) plasma having a ring of energetic electrons inside the chamber. The electrons bombard the x-ray emitter which in turn produces x-ray radiation in a given direction. A pair of magnetic members generate an axisymmetric magnetic mirror trap inside the chamber. The chamber may be nested within a microwave resonant cavity and between the magnets, or the chamber and microwave cavity may be a single composite structure. The source is useful to make x-ray photographs virtually anywhere and may be battery powered.

82 Claims, 3 Drawing Sheets

U.S. PATENT DOCUMENTS

Balmashov et al., "Passivation of GaAs by Atomic Hydrogen Flow Produced by the Crossed Beams Method" *Semicond. Sci. Technol*, 5 (1990) pp. 242–245.

Omeljanovsky et al. "Hydrogen Passivation of Defects and Impurities GaAs and InP" *J. Electronic Materials*, vol. 18, No. 6, 1989 pp. 659–670.

Popov, "An Electron Cyclotron Plasma Stream Source For Low Pressure Thin Film Production" *Surface and Coatings Technology*, 36 (1988) pp. 917–925.

Product Literature for ECR System 9200, Plasma Stream Sources Models 904, 904GR, 906, 906GR, 908, ECRI on Miller Model 1M601 ECRJr. Research System, by Microscience, five single pages and one tri-fold document.

Shapoval et al., "Cubic Boron Nitride Films Deposited by Electron Cyclotron Resonance Plasma" *Appl. Phys. Lett.* 57(18), 29 Oct. 1990, pp. 1885–85.

*Food Irradiation*, World Health Organization 1988, pp. 18–43.

Klinger et al., "Feed Radicidation in Israel–An Update," *Food Irradiation Processing Symposium Proceedings*, 4–8 Mar. 1985, pp. 117–126.

Krishnamurthy et al., "Design Considerations For Food Irradiators In Developing Countries" *Food Irradiation Processing Symposium Proceedings*, 4–8 Mar. 1985, pp. 353–363.

PORTABLE X-RAY SOURCE AND METHOD FOR RADIOGRAPHY

CROSS REFERENCE TO RELATED APPLICATIONS

This application is a continuation-in-part of U.S. patent application Ser. No. 07/843,569, entitled A Microwave X-Ray Source And Methods Of Sterilization, filed Feb. 28, 1992 in the names of Konstantin S. Golovanivsky and Valeri D. Dugar-Zhabon.

FIELD OF THE INVENTION

The present invention concerns an x-ray source for radiography, more particularly a portable x-ray source and methods for conducting medical, biological and industrial x-ray radiography.

BACKGROUND OF THE INVENTION

The existing equipment used for medical (and dental) x-ray radiography contains high voltage vacuum tubes and produce x-rays as a result of the bombardment of a target by electrostatically accelerated electrons. The electrical supplies for such tubes are based on high voltage ($\sim 100$ kilivolts) transformers. These transformers are very heavy, cumbersome, dangerous, and expensive pieces of equipment. Such conventional x-ray medical radiograph equipment is not portable and thus limits the use of the x-ray radiography in ambulances, distant areas, etc.

U.S. patent application Ser. No. 843,569, filed Feb. 18, 1992, which is copending and commonly assigned, the disclosure of which is incorporated herein by reference, describes an x-ray source that is based on an Electron Cyclotron Resonance (ECR) plasma. The ECR x-ray source is quite convenient to be used as a light, compact, safe and inexpensive low-voltage (but high enough photon energy and intensity) x-ray source. However, that ECR x-ray source has a large x-ray emitting surface which makes the resolution of the x-ray image poor and, without modification, not reasonably practicable for x-ray radiography, particularly in the medical field.

There remains a continuing need for better sources of x-rays for radiography. There also is a need for economical x-ray sources having sufficient intensity for radiography that are lightweight, portable, and may be operated from conventional energy supplies.

SUMMARY OF THE INVENTION

The present invention concerns an x-ray source based on an ECR plasma that, in contrast to the above ECR x-ray source of application Ser. No. 843,569, possesses acceptable x-ray image resolution features for use as an exceptionally light, compact and safe portable x-ray radiograph. It also concerns an x-ray source which is free of the above deficiencies and provides nearly the same x-ray intensity and energy as the classical high voltage x-ray sources, although it has a drastically smaller volume, weight, electrical consumption and cost. In addition, the x-ray source of the present invention produces an x-ray intensity that is sufficient to produce high quality x-ray images on conventional x-ray sensitive films, with about the same exposure time as conventional high voltage x-ray sources.

Broadly, the invention is directed to apparatus and methods for producing x-ray radiation by providing a vacuumated chamber that is filled with a plasma support gas at low pressure and an x-ray emitter, and exposing the chamber to a resonant electrical field and perpendicular magnetic field to generate an Electron Cyclotron Resonance (ECR) plasma inside the chamber. The plasma support gas preferably is a heavy atomic weight gas. The chamber is configured and the magnetic field is established so that the ECR plasma forms a ring of hot electrons which bombard the x-ray emitter. This bombardment, in turn, produces an x-ray emission from the emitter generally directed at a target. As used herein, the term target includes any object to be irradiated. Where the context permits, it also includes a primary target or object which is being studied, and a secondary target or object such as x-ray sensitive film to record an image of the primary.

In one preferred embodiment, the chamber is within a microwave resonant cavity and between a pair of magnetic members that generate an axisymmetric magnetic mirror trap inside the cavity and chamber. This produces an ECR plasma occurring on an axisymmetric hyperboloid sheet with a ring of hot electrons in the central part of the magnetic mirror trap. The electron ring provides a steady (or controllable) electron current which is received by the x-ray emitter, and thus produces a continuous x-ray emission on the emitter surface. If both the position and orientation of the emitter surface are appropriately selected, the emission will be outgoing, perpendicular to the magnetic field lines. The emission is at a sufficient intensity to irradiate an object and expose an x-ray sensitive film using conventional exposure times as explained below.

Advantageously, because of its small size, low cost, and low power requirements, the x-ray source of the present invention is easily manipulated, can be used in a conventional manner, and can be made portable to make x-ray photographs virtually anywhere. For example, in the case of medical x-ray radiographs, the x-ray source of the present invention can be conventionally used, e.g., in a hospital, doctor's or dentist's office. A portable device can be used to obtain x-ray images of injuries at the injury site, before the patient is moved or transported to another location. Thus, civilian and military rescue vehicles, e.g., ambulances, helicopters, fire engines and the like, can be equipped with the portable x-ray source of the present invention for use during emergencies, whether on a city street, in a desert, or in space. Similarly, in the case of x-ray radiography of structures, welds and other physical things, a portable x-ray source in accordance with the present invention can be easily used at the site where the object to be examined is located, e.g., at any time during construction of a structure such as a submarine, nuclear power facility or spacecraft. The present invention also can be used for non-medical radiography, such as for fault analysis and identification of paintings and other works of art in museums and art galleries.

BRIEF DESCRIPTION OF THE DRAWINGS

Further features of the invention, its nature and various advantages will be more apparent form the drawings and the following detailed description of the invention, in which like reference numerals refer to like elements, and in which.

DETAILED DESCRIPTION OF THE INVENTION

Figure 2:
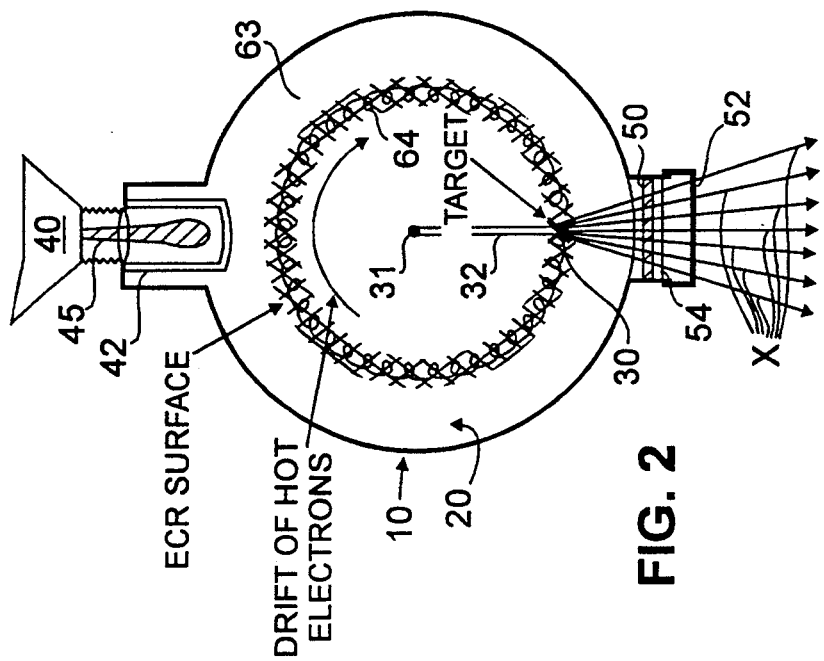
FIG. 2 shows an end cross-sectional view taken along line 2—2 of FIG. 1.

Referring to FIGS. 1-4, a preferred embodiment of the x-ray source for radiography in accordance with the present invention includes a microwave resonant cavity 10, a vacuumated discharge chamber 20, an x-ray emitter 30, a microwave energy source 40, a vacuum window 50, and a pair of magnetic members 61 and 62.

Figure 1:
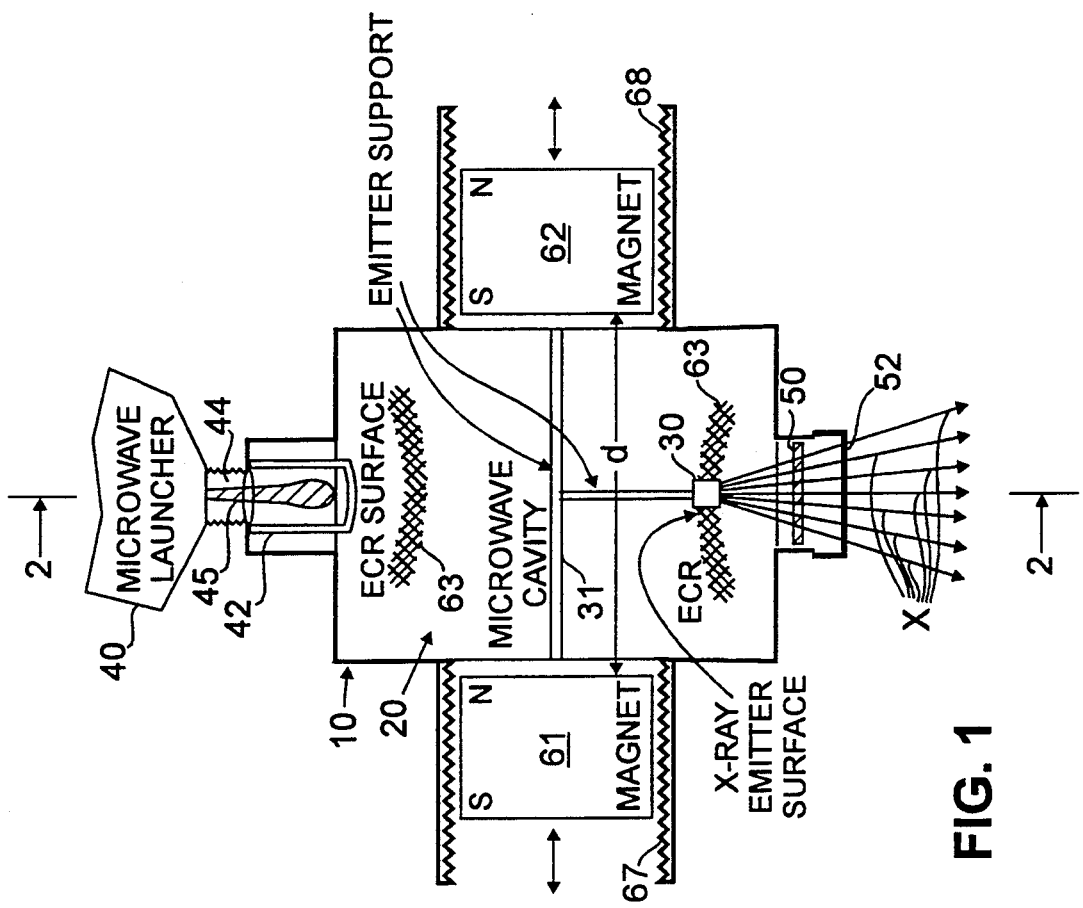
FIG. 1 shows a side cross-sectional schematic view of an x-ray source for radiography of the present invention, drawn to the scale indicated.

In the present invention, the x-ray is produced during the bombardment of a solid body, i.e., emitter 30, by an ECR plasma. The ECR plasma is created in a compact axisymmetric magnetic mirror trap which is formed by two permanent disk magnets, namely magnetic members 61 and 62. Members 61 and 62 are preferably symmetrically arranged about a midplane of chamber 20 with opposite poles, North N and South S, facing one another, as illustrated in FIG. 1.

If one applies in this magnetic field configuration an oscillating electrical field perpendicular to the magnetic field lines, then the phenomenon of the ECR can occur. The condition to be satisfied for an ECR condition is:

$$\omega = eB/mc \text{ (CGS units)}$$

where $\omega$ is the circular frequency of the oscillating (microwave) field, m and e are respectively the mass and the charge of an electron, c is the light speed in free space, and B is the magnetic induction.

In an axisymmetric magnetic mirror with the field value in the geometric center slightly exceeding the ECR value at the given microwave frequency (which is feasible if strong enough magnetic members 61, 62 are used), the ECR phenomenon occurs on a axisymmetric physical surface resembling a hyperboloid of one sheet. This is illustrated in section by the double cross hatched curves labeled 63 on FIGS. 1 and 4.

If a gas at low pressure fills the area in discharge chamber 20 between magnets 61 and 62, then an ECR plasma starts up. The electrons on the ECR surface 63 acquire high energy, ranging from between 50 and 200 keV depending on the microwave power applied. The electrons are accumulated near the midplane of the mirror configuration due to the action of the magnetic mirrors. As a result a hot electron ring 64 is built up in the central part of the magnetic mirror trap. This is illustrated by the black dots labeled 64 on FIG. 4 and the helical strand labeled 64 in FIG. 3.

Figure 3:
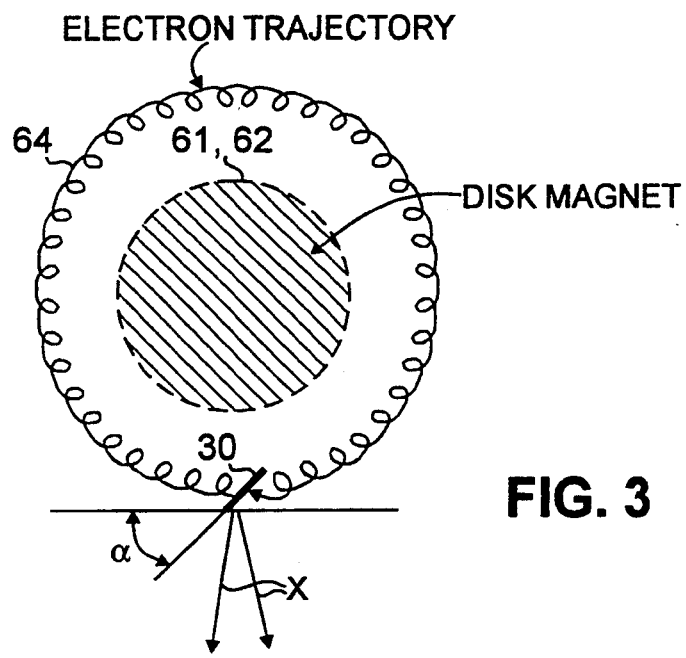
FIG. 3 shows a schematic view of the azimuthal drift of electrons due to the radial gradient of the magnetic field of the source of FIG. 1.
Figure 4:
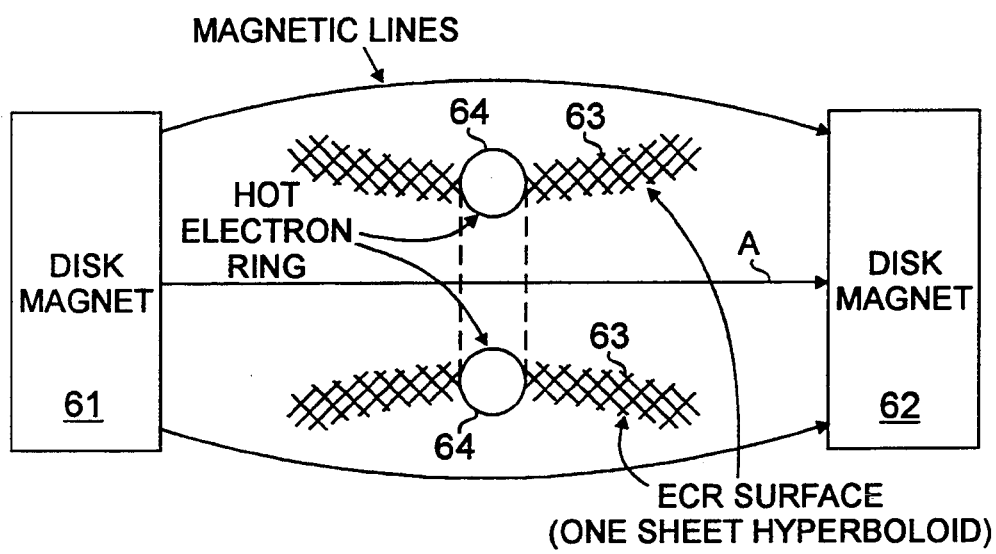
FIG. 4 shows a side schematic view of the hot electron ring formation in an ECR supplemented magnetic mirror configuration in accordance with the present invention.

In the midplane of an axisymmetric magnetic mirror trap the magnetic field strength decreases when moving from the axis to the periphery. Consequently, a well known phenomenon of the "gradient drift" occurs, as described in, for example, F. F. Chen *Introduction to Plasma Physics and Controlled Fusion*, Plenum Press, New York and London, 1984. Due to this phenomenon, the electron Larmor orbit in the hot electron ring 64 drifts azimuthally so that every electron participates in two rotations: first one around the field line and second one around the axis passing azimuthally from one field line to another. This is illustrated in FIG. 3. This azimuthal drift allows a small body, i.e., emitter 30, intersecting the ring 64, to "catch" all the hot electrons. Since the period of the azimuthal rotation is very short, i.e., 0.1 to 3 $\mu$s, most if not all of the electrons are received by (i.e., bombard) the emitter 30, rather than being pushed to the periphery due to the flute instability. The latter phenomenon occurs in the ECR x-ray source described in application Ser. No. 843,569, where there is no emitter body interposed in the electron current flow.

Thus, in the present invention, emitter 30 receives a permanent, i.e., continuous, current of very energetic electrons once the plasma is ignited and maintained. As a result, a permanent, i.e., continuous, x-ray emission is produced on the surface of emitter 30. The emission is outgoing perpendicular to the magnetic lines, as illustrated by the arrows labeled x on FIGS. 1-3, if both the position and orientation of the emitter surface are appropriately chosen. Preferably, emitter 30 is inside the hot electron ring. The optimal orientation is empirically obtained to provide the desired direction of the x-ray beam emission.

In one embodiment, the microwave resonant cavity 10 and the vacuumated discharge chamber 20 are formed as a unitary composite structure, namely a vacuumated microwave resonant cavity which also serves as a discharge chamber filled with the plasma support gas at low pressure. Alternatively, the chamber 20 may be enveloped by cavity 10, in which case cavity 10 need not be vacuumated. Advantageously, in either embodiment, the gas and emitter 30 may be sealed inside either chamber 20 or a combined cavity 10/chamber 20 and provided as a replaceable cartridge for the x-ray source that has a useful life, and which can be easily replaced when its usefulness is consumed. Referring now to FIGS. 1 and 2, one embodiment of the present invention is described in which microwave resonant cavity 10 is vacuumated and also serves as discharge chamber 20. Cavity 10 is preferably a metallic cylinder (other shapes are also possible) having an axis A inside of which a metallic emitter 30 is fixed in the midplane between axis A and the wall. The axis A is shown on FIG. 4. Emitter 30 is securely suspended from support 31, which preferably lies in the midplane of cavity 10, and is oriented at an angle $\alpha$ (see FIG. 3) of between 15 and 75 degrees, preferably between 70 and 75 degrees, relative to the tangent of electron ring 64, and in a plane perpendicular to the plane of electron ring 64. Supports 31 and 32 are transparent to the microwave energy and the magnetic field and are made of, e.g., quartz, quartz glass, or a ceramic. Supports 31 and 32 also may be made of non-magnetic metals, e.g., tantalum, molybdenum, and stainless steel, arranged perpendicular to the electric field lines.

Cavity 10/chamber 20 is filled with a gas at a low pressure and is placed between two magnetic members 61 and 62. Members 61 and 62 are preferably permanent magnets, aligned coaxially with and spaced equidistantly about the midplane of the cavity on axis A. Members 61 and 62 also may be made of electro-magnets or solenoids. Permanent magnets are preferred because they are compact, light in weight, and do not consume electrical energy to generate the magnetic mirror.

The distance d between magnets 61 and 62 is adjustable and is chosen in such a manner that the ECR surface 63 becomes a one-sheet hyperboloid and emitter 30 is effectively positioned to enter and intersect the ECR surface 63 from inner side, as illustrated in FIG. 1. In this regard, selecting the distance d controls the magnetic mirror field profile and, hence, the relative location and shape of ECR surface 63 inside chamber 20, and controls the optimum conditions to ignite the plasma on start up and to maintain the plasma and x-ray emission during continued operation. Adjustment may be achieved, for example, rotating magnets 61 and 62 in cooperating threaded recesses 67 and 68 on opposite sides of chamber 20 (FIG. 1). However, in as much as most radiographic procedures have exposure times on the order of seconds, once an x-ray source is tuned for a sustained plasma, no adjustment may be required during continued operation.

The x-ray coming from emitter 30 outgoes through a vacuum window 50. Window 50 may be mechanically protected by a rigid protective cover 52. Window 50 is presented facing the target or object to be irradiated, e.g., the patient during a medical radiographic procedure. Both window 50 and any cover 52 are transparent for the x-ray.

Cavity 10 has a conventional electrically conductive material on its inside surface and is fed microwave energy through a vacuum window 42 using any conventional technique. FIG. 1 illustrates one coupling using a coaxial cable 44 and an electrical field antenna 45 introduced in the volume of cavity 10 without deterioration of the vacuum conditions. Since the exposure time is quite short (on the order of seconds) there is no appreciable concern of heating window 42 or any related difficulties. In this regard, window 42 is made of a microwave transparent material that is capable of sustaining the low pressure inside chamber 20, e.g., quartz, quartz glass or a ceramic. In an alternate embodiment, where cavity 10 is not vacuumated, window 42 may be omitted.

Chamber 20 may be filled with the heavy, chemical-passive gas in a well-known manner, for example, by evacuating chamber 20 on a commercially available vacuum pump, at an elevated temperature, to out gas any impurities in the chamber material. The chamber is then filled with the gas and the tubulation used for out-gassing and filling is sealed. If chamber 20 is not a part of cavity 10, it may be made of a dielectric material that is transparent to microwave energy, magnetic fields and x-ray radiation, e.g., quartz, quartz glass or a ceramic.

Cavity 10, when also serving as discharge chamber 20, has to be made of a highly conductive metal which, after a conventional treatment during fabrication, is not outgasing during a long time. Another requirement, whether or not it also serves as discharge chamber 20, is that it provide good protection for the operator against the x-ray radiation, which can penetrate through the resonant cavity walls. Accordingly, the conductive metal is coated with a 2 mm thick copper layer which is in turn covered by a 2 mm thick lead layer. The copper provides good thermal conductivity to minimize localized heating, and the lead provides x-ray absorption.

To ignite and maintain a hot electron plasma, cavity 10 has to be fed sufficient microwave energy. Since the minimum diameter of cavity 10 is of the order of the microwave wavelength, the latter should be chosen in the range of 10 cm in order to have a portable device which is convenient to handle physically, and may be handheld. A large choice of inexpensive microwave power sources in the frequency band of 2.45 GHz (corresponding to a wavelength of 12.2 cm) are available and may be used as the working frequency.

The needed microwave power from source 40 is based upon the sensitivity of the available medical x-ray film. Standard x-ray film sensitivity is typically 1.0 milliwatt per $cm^2$ per second. To obtain a photograph of 100 $cm^2$ one needs 0.1 watt of x-ray during 1.0 second. To obtain such an x-ray power emitted by emitter 30 made of tungsten, at the electron energy of 100 keV, one has to dissipate on the surface of emitter 30 an electron flux power of to 15 watts (W. J. Price, *Nuclear radiation detection*, McGraw Hill Book Company Inc., N.Y.,-Toronto, London, 1958, p. 19).

At the electron energy of 100 keV, an electron current of only 150 micro-amperes on the surface of emitter 30 produces a power of 15 watts. This amount of electron current is usually produced in ECR plasmas without requiring any special operating conditions. Supposing that one-half of the energy stored in the ECR plasma discharge is accumulated in the electron ring 64 and that the other half of the microwave energy is absorbed by the ECR discharge plasma, a microwave power of 100 watts is sufficient for a normal operation of the portable medical x-ray imaging apparatus of the present invention. A power range of 50 to 1,000 watts is believed suitable for most medical x-ray imaging for exposing standard film sizes of 100 to 1,000 $cm^2$. One such power supply may provide an adjustable range, e.g., between 200-500 watts, or between 50 and 300 watts, etc.

The discharge chamber 20 (i.e., the interior microwave cavity 10) has to be filled by a plasma support gas in order to produce an ECR plasma providing energetic electrons. The requirements are that the support gas not interact with the walls of chamber 20, have a large atomic mass to reduce plasma losses, and have a low ionization potential to ignite and sustain easily an ECR plasma. Suitable gases are the heavy noble gases, such as argon, krypton or xenon gases. The gas is preferably sealed inside chamber 20 at a desired low pressure in the range of $10^{-3}$ to $10^{-6}$ Torr, preferably $1 \times 10^{-5}$ to $4 \times 10^{-4}$ Torr, and more preferably $9 \times 10^{-5}$ to $4 \times 10^{-4}$ Torr. It is to be understood that the interior conductive layer of cavity 10 may be coated with a material that will not react with the plasma support gas, and permit the forming of ECR plasma, if necessary.

In the case that the magnetic members 61 and 62 are permanent magnets, they are secured in parallel about cavity 10 separated by a distance d along axis A. Accordingly, their magnetic field strength should be sufficient to produce in the central point of the cavity a magnetic induction value $|B|$ exceeding the ECR value for the selected microwave frequency.

If a frequency of 2.45 GHz is used, the magnetic induction $|B|$ in the central point is preferably not lower than 1 kG (the ECR value is 0.865 kG). At a typical distance d of 10 cm, magnetic members 61 and 62 each may be made in the form of a disk of 5 cm diameter and 2 cm thick, from such widely used and inexpensive magnetic materials as samarium-cobalt or neodymium-ferrum-boron. Such magnetic disks 61 and 62 produce the needed magnetic induction without difficulty or adverse consequences.

Emitter 30 is preferably a solid body, more preferably a metallic plate for receiving energetic electrons and converting some of their energy into the x-ray. The choice of the emitter material is determined by two requirements: the conversion rate has to be maximal and the non-converted energy (thermal) should not damage emitter 30. To satisfy both conditions the material chosen must have a relatively large atomic number and high melting temperature. Preferred metals for emitter 30 are tungsten and tantalum. Any other material that satisfies these conditions may be used. Thus, a tungsten or tantalum plate emitter 30 electrode that is 5 mm×5 mm and 1 mm thick will in practice satisfy these requirements.

Window 50 plays a double role. First, it allows x-ray radiation to pass to the target. Second, it preserves the vacuum in chamber 20. To accomplish both functions, the material of the window must have as low an atomic number as possible, be rigid mechanically, and be a good vacuum material. Suitable materials for window 50 include light element metals, quartz, aluminum, and plastics, preferably beryllium or aluminum. Cover 52, when used, may be any rigid x-ray transparent material, such as plastic, plexiglass, or polyethylene. Cover 52 may be spaced a distance from window 50 that is selected to correspond to the area of the target to be irradiated by the x-rays and placed in touching contact with the target. This provides for accurate alignment of the area of target to be exposed with the x-ray. The distance between window 50 and cover 52 also may be selected to provide a spacing in the nature of a focal length (or plane) for irradiating the target with a controlled x-ray beam area and intensity.

As shown in FIGS. 1 and 2, window 50 is a round cross-sectional area that is in a flat plane spaced a distance of about 1.0 cm from the circumference of chamber 20 and cover 52 is secured about 1.0 cm from window 50 in a parallel flat plane. Other shapes, spacings, and contoured planes for window 50 and cover 52 may be used.

Window 50 also may be provided with a shutter 54 that absorbs the x-ray radiation and when open, permits x-ray transmission (not shown). This may be used to absorb x-ray emissions until the plasma has reached a steady state condition after startup. The shutter also may be used for time lapse exposure for a sequence of x-ray images are desired, e.g., to prepare a motion picture of some event or activity, or to obtain a large number of images in rapid succession.

EXAMPLE

Figure 5:
FIG. 5 is an image of an x-ray photograph taken using a prototype of the invention in accordance with FIGS. 1-3.

A prototype x-ray source for medical radiographic procedures in accordance with the source illustrated in FIGS. 1-4 was built and tested. The parameters for one construction of the prototype were as follows. The microwave resonant cavity 10, which also served as discharge chamber 20, was vacuumated. It had a diameter of 13 cm, a height of 9 cm (measured along axis A). The cavity 10/chamber 20 was a composite unitary structure made of a layer of aluminum 5 mm thick and an outer layer of either stainless steel 5.0 mm thick or lead 2.5 mm thick. It was filled with argon gas at a pressure of $2\times10^{-5}$ Torr. The window 50 was 40 mm in diameter and 12 mm thick and made of a commercial PLEXIGLASS material. The emitter 30 was a 4 mm ×4 mm×1 mm tantalum plate. It was positioned at an angle of 15 degrees relative to the direction of the radius passing through the center of the emitter plate and was spaced 10 mm from axis A in the midplane of cavity 10/chamber 20. The microwave source 40 was a magnetron at 2.45 GHz and produced 150 watts. An image of an x-ray (70 cm² having a diameter of about 9.4 cm) of a rat taken using the prototype at an exposure time of 2 seconds is illustrated in FIG. 5. No light amplifier was used.

Another prototype x-ray source has the following construction parameters. The cavity 10/chamber 20 of the same dimensions was a unitary structure having a layer of aluminum 10 mm thick and filled with argon gas at $2\times10^{-5}$ Torr. The window was made of a commercial PLEXIGLASS material that was 85 mm in diameter. The emitter was a 4 mm ×4 mm×1 mm tantalum plate positioned at an angle of 45° relative to the window axis and was spaced 15 mm from axis A in the midplane of cavity 10/chamber 20. The same microwave source and power is used.

Another aspect of the invention is directed to a source and a method for irradiating body tissue with x-rays at a dosage level and for a time sufficient for medical or dental diagnostic or therapeutic purposes. This includes fluoroscopy and exposing x-ray film. Such methods include generating an ECR plasma to produce x-rays in a given direction, for example, in a given solid angle, to expose a film for x-ray evaluation of tissue, bone and other physical structures. These exposure methods include mammography and computer aided tomography (CAT scans). Such methods also include generating an ECR plasma to produce x-rays for medical therapeutics, for example, cancer therapy, diathermy, and activating x-ray responsive drugs. In this regard, the x-ray dosages to be used are those generally used in medical and dental diagnostic and therapeutic practices. Advantageously, the small and light weight of the x-ray source of the present invention, together with a lead shield that covers all of the cavity except suitably shaped window 50, provide easy maneuverability to locate the source proximate to the subject and easy portability of the apparatus, for example, for a mobile medical clinic. In addition, the small size, simplicity of operation, and low power requirements permit providing emergency service vehicles such as ambulances, fire rescue vehicles and the like with portable x-ray machines, which may be hand held and battery powered, for obtaining x-ray images of injured patients prior to moving them. In this regard, the x-ray source may include a battery power supply or be powered by the alternator of a vehicle or a generator or line current (110 volt). A suitable rechargeable battery would require a 12 volt and 10 amp-hour capacity which could provide approximately fifty x-ray film exposures before requiring a recharge. A 24-volt battery having a 50 amp-hour charge would provide a longer useful life before requiring a recharge and higher power output levels.

One skilled in the art will appreciate that the present invention can be practiced by other than the described embodiments which are presented for purposes of illustration and not of limitation.

I claim:
1. Apparatus for use in x-ray imaging comprising:
   a vacuumated plasma discharge chamber containing a plasma support gas at a selected low pressure;
   a magnetic field system having a pair of permanent magnets for producing an axisymmetric magnetic mirror inside the plasma discharge chamber;
   a microwave resonant cavity for supporting an oscillating electric field perpendicular to the magnetic field inside the plasma discharge chamber to form a plasma in the form of a hyperboloid for one sheet including hot electrons under electron cyclotron resonance conditions;

a microwave source for supplying microwaves to the microwave resonant cavity; and an x-ray emitter structure positioned inside the chamber to intersect the formed hot plasma electrons, thereby to produce x-ray radiation in response to the plasma being formed.

2. The apparatus of claim 1 wherein the cavity and chamber are a unitary composite structure having an inner layer of electrically conductive material, a layer of a first material superimposed about the inner layer for containing x-ray radiation, and a window in a portion of the structure made of a material that is transparent to x-ray radiation and is mechanically rigid to maintain the chamber vacuumated at the selected pressure.

3. The apparatus of claim 2 wherein the first material is a 2 mm thick layer of lead.

4. The apparatus of claim 3 further comprising a 2 mm thick layer of copper interior to the layer of lead.

5. The apparatus of claim 2 wherein the window further comprises a material selected from among the group consisting of beryllium, quartz, aluminum, and plastic.

6. The apparatus of claim 2 wherein the unitary composite structure further comprises a protective cover disposed over the window made of a material transparent to x-ray radiation.

7. The apparatus of claim 6 wherein the protective cover further comprises a plastic.

8. The apparatus of claim 1 wherein the chamber is located inside the cavity and the cavity further comprises:

a layer of an electrically conductive material for containing microwaves;

a layer of a first material for containing x-ray radiation, disposed about the electrically conductive layer; and a window in the layer of first material for passing x-ray radiation out of the chamber in a given direction.

9. The apparatus of claim 8 wherein the first material is a 2 mm thick layer of lead.

10. The apparatus of claim 9 wherein the cavity further comprises a 2 mm thick layer of copper interior to the layer of lead.

11. The apparatus of claim 8 wherein the window further comprises a material selected from among the group consisting of beryllium, quartz, aluminum, and plastic.

12. The apparatus of claim 8 wherein the window further comprises a protective cover made of a material transparent to x-ray radiation.

13. The apparatus of claim 12 wherein the protective cover layer further comprises a plastic.

14. The apparatus of claim 2 wherein the x-ray emitter structure is oriented so that the x-ray radiation is emitted perpendicularly to the magnetic field and outwardly from the chamber through the window.

15. The apparatus of claim 8 wherein the x-ray emitter structure is oriented so that the x-ray radiation is emitted perpendicularly to the magnetic field and outwardly from the chamber through the window.

16. The apparatus of claim 8 wherein the microwave resonant cavity is non-vacuumated.

17. The apparatus of claim 1 wherein the pair of permanent magnets are disposed in axial alignment and in polar opposition on opposite sides of the discharge chamber.

18. The apparatus of claim 1 wherein the chamber is cylindrical in shape.

19. The apparatus of claim 17 wherein the distance between the magnets is adjustable.

20. The apparatus of claim 19 wherein the magnets are made of $SmCo_5$ and have a magnetic induction on the surface on the order of 0.4 Tesla.

21. The apparatus of claim 2 wherein the unitary composite structure further comprises a second window, made of a material that is transparent to microwave energy and will maintain the composite unitary structure vacuumated at the selected pressure, for receiving microwave energy into said unitary structure.

22. The apparatus of claim 1 wherein the gas is present in the chamber at a selected pressure of from between $10^{-3}$ and $10^{-5}$ Torr.

23. The apparatus of claim 1 wherein the gas is selected from among heavy atomic weight gases.

24. The apparatus of claim 23 wherein the gas is selected from among the group consisting of argon, krypton, and xenon.

25. The apparatus of claim 1 wherein the x-ray emitter structure is a metallic plate having a large atomic number and a high melting structure.

26. The apparatus of claim 25 wherein the plate is made of one of tantalum and tungsten.

27. The apparatus of claim 1 further comprising a microwave power source for delivering microwave energy to the cavity for a time and at a power level sufficient to expose a film of x-ray sensitive material.

28. The apparatus of claim 27 wherein the x-ray emitter structure is a metallic plate having a large atomic number and a high melting temperature, the selected pressure is from between $10^{-3}$ and $10^{-5}$ Torr, and the deliverable microwave energy is in the range from 50 to 1,000 watts at a frequency of 2.45 GHz.

29. The apparatus of claim 2 further comprising a shutter over the window having an open position for passing x-ray radiation and closed position for absorbing x-ray radiation.

30. A method for use in x-ray imaging comprising:
providing a sealed plasma discharge chamber with a plasma support gas at a selected low pressure;
placing an x-ray emitter structure inside the plasma discharge chamber;
applying a magnetic field to the discharge chamber;
supplying microwaves to the discharge chamber, said microwaves producing an oscillating electric field perpendicular to the magnetic field;
exposing the chamber to the magnetic field and the oscillating electric field;
forming a plasma in the form of a hyperboloid of one sheet from the support gas, including hot electrons, under ECR conditions; and
bombarding the x-ray emitter continuously with hot electrons to produce x-ray radiation in response to the plasma being formed.

31. The method of claim 30 wherein placing the x-ray emitter further comprises orienting the emitter so that the x-ray radiation is emitted perpendicularly to the magnetic field and outwardly from the chamber in a given direction.

32. The method of claim 30 wherein exposing the chamber to a magnetic field further comprises producing an axisymmetric magnetic mirror field inside the plasma discharge chamber.

33. The method of claim 32 further comprising adjusting the magnetic mirror field inside the plasma discharge chamber to control the bombardment of the x-ray emitter by hot electrons.

34. The method of claim 33 wherein providing and adjusting the magnetic mirror field further comprise providing a pair of magnetic members axially spaced on opposite sides of the chamber and selecting the distance to control forming the plasma and bombarding the x-ray emitter with hot electrons.

35. The method of claim 34 wherein providing the pair of magnetic members further comprises providing a pair of permanent magnets and orienting the magnets with opposite poles facing one another.

36. The method of claim 34 further comprising forming the magnets of $SmCo_5$ with a magnetic induction on the surface on the order of 0.4 Tesla.

37. The method of claim 30 wherein providing a vacuumated plasma discharge chamber further comprises providing a unitary composite structure having an inner electrically conductive material, a first material superimposed outwardly of the inner material for containing x-ray radiation, and a window in a portion of the structure made of a material that is transparent to x-ray radiation and mechanically rigid to maintain the chamber vacuumated at the selected pressure.

38. The method of claim 37 wherein the first material is a 2 mm thick layer of lead.

39. The method of claim 38 further comprising interposing a 2 mm thick layer of copper interior to the layer of lead.

40. The method of claim 37 wherein the window further comprises a material selected from among the group consisting of beryllium, quartz, aluminum, and plastic.

41. The method of claim 39 further comprising covering the window with a protective material transparent to x-ray radiation.

42. The method of claim 30 wherein exposing the chamber to an oscillating electric field further comprises inserting the chamber inside a microwave resonant cavity having a layer of electrically conductive material for containing microwaves, a layer of a first material outwardly of the conductive material for containing x-ray radiation, and a window in the first layer of material for passing x-ray radiation therethrough.

43. The method of claim 42 wherein the first material is a 2 mm thick layer of lead.

44. The method of claim 42 further comprising interposing a 2 mm thick layer of copper interior to the layer of lead.

45. The method of claim 42 wherein the window further comprises a material selected from among the group consisting of beryllium, quartz, aluminum, and plastic.

46. The method of claim 42 further comprising covering the window with a protective material transparent to x-ray radiation.

47. The method of claim 30 further comprising delivering microwave energy to the cavity for a time and at a power level sufficient to expose a film of x-ray sensitive material.

48. The method of claim 37 wherein placing the x-ray emitter further comprises orienting the emitter so that the x-ray radiation is emitted perpendicularly to the magnetic field and outwardly from the chamber through the window.

49. The method of claim 42 wherein placing the x-ray emitter further comprises orienting the emitter so that the x-ray radiation is emitter perpendicularly to the magnetic field and outwardly from the chamber through the window.

50. The method of claim 42 wherein the microwave resonant cavity is non-vacuumated.

51. The method of claim 37 wherein providing the unitary structure further comprises providing a second window in the structure, made of a material that is transparent to microwave energy and will maintain the chamber vacuumated at the selected pressure, for passing microwave energy into the structure.

52. The method of claim 30 wherein the gas is present in the chamber at a selected pressure of from between $10^{-3}$ and $10^{-5}$ Torr.

53. The method of claim 52 wherein the gas is selected from among heavy atomic weight gases.

54. The method of claim 53 wherein the gas is selected from among the group consisting of argon, krypton, and xenon.

55. The method of claim 30 wherein the x-ray emitter is a metallic plate having a large atomic number and a high melting temperature.

56. The method of claim 55 wherein the x-ray emitter is one of tantalum and tungsten.

57. The method of claim 47 wherein the x-ray emitter is a metallic plate having a large atomic number and a high melting temperature, the selected pressure is from between $10^{-4}$ and $10^{-5}$ Torr, and providing microwave energy further comprises providing a microwave energy at a frequency of 2.45 GHz for a time on the order of seconds and an energy selected from the range of between 50 and 1,000 watts.

58. The method of claim 56 further comprising providing a microwave energy source and a battery for operating the microwave energy source.

59. The method of claim 58 further comprising providing the chamber with a cylindrical shape.

60. An x-ray source comprising a plasma discharge chamber, a microwave source for supplying microwaves to the plasma discharge chamber, a magnetic field system for producing an axisymmetric magnetic mirror inside the plasma discharge chamber, and an electron cyclotron resonance plasma and an x-ray emitter structure disposed within the chamber, wherein the plasma is in the form of a hyperboloid of one sheet containing an electron current flow and the emitter structure is fixed in the path of the electron current flow.

61. An x-ray source as in claim 60, wherein the chamber volume is on the order of 1200 $cm^3$.

62. An x-ray source as in claim 60, wherein the chamber is sealed and the pressure within the chamber is $10^{-5}$ to $10^{'3}$ Torr.

63. An x-ray source as in claim 60, wherein the chamber is cylindrical in shape.

64. An x-ray source as in claim 60, wherein the electron cyclotron resonance plasma is a heavy atomic weight gas.

65. An x-ray source comprising a nonvacuumated microwave resonant cavity, a microwave source for supplying microwaves to the microwave resonant cavity, a sealed chamber within the cavity, a magnetic field system for producing an axisymmetric magnetic mirror inside the sealed chamber, said sealed chamber containing an electron cyclotron resonance plasma in the form of a hyperboloid of one sheet and an x-ray emitter body, wherein the plasma intersects the x-ray emitter body.

66. An x-ray source as in claim 65 wherein the plasma intersects the x-ray emitter.

67. An x-ray source as in claim 65, wherein the chamber is cylindrical in shape.

68. An x-ray source as in claim 65, wherein the chamber contains a hot electron ring that intersects the emitter body, thereby to produce x-rays.

69. A source for use in generating x-rays comprising a vacuumated sealed chamber containing a heavy atomic weight gas or gas mixture at a pressure of $10^{-5}$ to $10^{-33}$ Torr and an x-ray emitter capable of producing x-rays in response to bombardment by hot electrons, a microwave source for supplying microwaves to the sealed chamber, a magnetic field system for producing an axisymmetric magnetic mirror inside the sealed chamber, wherein the gas in the sealed chamber forms a plasma in the form of a hyperboloid of one sheet under electron cyclotron resonance conditions containing a closed electron ring which bombards the emitter.

70. The source as in claim 69 wherein the chamber interior is an electrically conductive material for containing an oscillating electric field.

71. The source in claim 70 wherein the chamber further comprises a layer of material for containing x-ray radiation superimposed over a first portion of the chamber interior and a window superimposed over a second portion of chamber interior for passing x-rays therethrough.

72. The source as in claims 69 wherein the chamber volume is on the order of 1200 cm$^3$.

73. The source as in claim 69 wherein the chamber is cylindrical.

74. The source as in claim 69 wherein the chamber is made of a dielectric material transparent for microwave energy.

75. Apparatus for use in x-ray imaging comprising:
a vacuumated plasma discharge chamber containing a plasma support gas;
a magnetic field system for producing an axisymmetric magnetic mirror inside the plasma discharge chamber;
a microwave source for supplying microwaves to the plasma discharge chamber,
a resonant cavity for supporting an oscillating electric field perpendicular to the magnetic field inside the plasma discharge chamber to form a plasma in the form of a hyperboloid of one sheet including hot electrons under electron cyclotron resonance conditions, wherein the diameter of the resonant cavity is on the order of the wavelength of the microwaves;
and an x-ray emitter structure positioned inside the plasma discharge chamber to intersect the formed hot plasma electrons, thereby to produce x-ray radiation in response to the plasma being formed.

76. The apparatus of claim 75 wherein the magnetic field system comprises a pair of permanent magnets.

77. The apparatus of claim 75 and wherein the resonant cavity is a microwave resonant cavity.

78. Apparatus for use in x-ray imaging comprising:
a vacuumated plasma discharge chamber containing a plasma support gas;
a magnetic field system for producing an axisymmetric magnetic mirror inside the plasma discharge chamber;
a microwave source for supplying microwaves to the plasma discharge chamber;
a resonant cavity for supporting an oscillating electric field perpendicular to the magnetic field inside the plasma discharge chamber to form a plasma in the form of a hyperboloid of one sheet including hot electrons under electron cyclotron resonance conditions, wherein the length of the resonant cavity is on the order of the wavelength of the microwaves;
and an x-ray emitter structure positioned inside the plasma discharge chamber to intersect the formed hot plasma electrons, thereby to produce x-ray radiation in response to the plasma being formed.

79. The apparatus of claim 78 wherein the magnetic field system comprises a pair of permanent magnets.

80. The apparatus of claim 78 wherein the resonant cavity is a microwave resonant cavity.

81. Apparatus for use in x-ray imaging comprising:
a vacuumated plasma discharge chamber containing a plasma support gas;
a magnetic field system having a pair of permanent magnets for producing an axisymmetric magnetic mirror inside the plasma discharge chamber;
a resonant cavity for supporting an oscillating electric field perpendicular to the magnetic field inside the plasma discharge chamber to form a plasma in the form of a hyperboloid of one sheet including hot electrons under electron cyclotron resonance conditions;
a microwave source for supplying microwaves to the plasma discharge chamber; and
an x-ray emitter structure positioned inside the chamber to intersect the formed hot plasma electrons, thereby to produce x-ray radiation in response to the plasma being formed.

82. The apparatus of claim 81 and wherein the resonant cavity is a microwave resonant cavity.

* * * * *